US012800524B2

(12) United States Patent
Otsuka et al.

(10) Patent No.: US 12,800,524 B2
(45) Date of Patent: Nov. 17, 2026

(54) ELECTRON MICROSCOPE AND CRYSTAL EVALUATION METHOD

(71) Applicant: Kioxia Corporation, Tokyo (JP)

(72) Inventors: Yuki Otsuka, Yokkaichi Mie (JP); Ken Hoshino, Yokkaichi Mie (JP); Haruko Akutsu, Yokosuka Kanagawa (JP)

(73) Assignee: KIOXIA CORPORATION, Tokyo (JP)

( * ) Notice: Subject to any disclaimer, the term of this patent is extended or adjusted under 35 U.S.C. 154(b) by 282 days.

(21) Appl. No.: 18/583,333

(22) Filed: Feb. 21, 2024

(65) Prior Publication Data

US 2024/0319122 A1 Sep. 26, 2024

(30) Foreign Application Priority Data

Mar. 20, 2023 (JP) ................................. 2023-044775

(51) Int. Cl.
*G01N 23/203* (2006.01)
*G01N 23/20025* (2018.01)
*G01N 23/2055* (2018.01)
*G01N 33/204* (2019.01)

(52) U.S. Cl.
CPC ..... *G01N 23/203* (2013.01); *G01N 23/20025* (2013.01); *G01N 23/2055* (2013.01); *G01N 33/204* (2019.01)

(58) Field of Classification Search
CPC ............... G01N 23/203; G01N 23/204; G01N 23/20025; G01N 23/2055
See application file for complete search history.

(56) References Cited

U.S. PATENT DOCUMENTS 12,099,024 B2 * 9/2024 Day ..................... G01N 23/203
2014/0291511 A1 * 10/2014 Man .................... H01J 37/3002 250/307
2015/0369760 A1 * 12/2015 Penman ............... G01N 23/203 250/307
2016/0216219 A1 * 7/2016 Wright ............. G01N 23/20058
(Continued)

FOREIGN PATENT DOCUMENTS

JP 2009-264750 A 11/2009
JP 2017-110935 A 6/2017
(Continued)

*Primary Examiner* — David E Smith
(74) *Attorney, Agent, or Firm* — Foley & Lardner LLP

(57) ABSTRACT

An electron microscope includes an electron beam irradiation unit, a subject holding unit that has a subject installation surface, and a second detection unit that detects an EBSD image. In addition, the electron microscope includes an SEM control unit that controls an operation of the subject holding unit, and an EBSD analysis unit that analyzes a crystal structure of a subject based on the EBSD image. The subject holding unit is rotatable around an axis parallel to a direction of irradiation with an electron beam, and is configured such that the subject installation surface is inclinable with respect to a plane perpendicular to the direction of irradiation with the electron beam. The EBSD analysis unit has an MAD value calculation unit that calculates a degree of similarity between the EBSD image and a reflector, and the SEM control unit controls a rotation operation or an inclination operation of the subject holding unit based on the degree of similarity.

8 Claims, 7 Drawing Sheets

(56) References Cited

U.S. PATENT DOCUMENTS

| | | | | |
|---|---|---|---|---|
| 2020/0066480 | A1* | 2/2020 | Amino .................. | H01J 37/265 |
| 2022/0230844 | A1* | 7/2022 | Dobashi ................ | H01J 37/265 |

FOREIGN PATENT DOCUMENTS

| | | | |
|---|---|---|---|
| JP | 2020-085448 | A | 6/2020 |
| JP | 2022-054823 | A | 4/2022 |
| WO | WO-2020/235091 | A1 | 11/2020 |

* cited by examiner

ELECTRON MICROSCOPE AND CRYSTAL EVALUATION METHOD

CROSS-REFERENCE TO RELATED APPLICATION

This application is based upon and claims the benefit of priority from Japanese Patent Application No. 2023-044775, filed Mar. 20, 2023, the entire contents of which are incorporated herein by reference.

FIELD

Embodiments described herein relate generally to an electron microscope and a crystal evaluation method.

BACKGROUND

In the development of semiconductor devices, it is important to analyze the crystallinity in a minute area. As a device for analyzing the crystallinity in a minute area, an electron microscope including an EBSD detector is known.

DETAILED DESCRIPTION

At least one embodiment provides an electron microscope and a crystal evaluation method capable of efficiently and accurately analyzing crystallinity.

In general, according to at least one embodiment, there is provided an electron microscope that includes an electron beam irradiation unit (electron beam irradiation source) that irradiates an irradiation area of a surface of a subject with an electron beam, and a subject holding unit (subject holder) that has a subject installation surface on which the subject is placed. In addition, the electron microscope of the present embodiment includes a first detection unit (first detector) that detects secondary electrons emitted from the subject by irradiation with the electron beam, and a second detection unit (second detector) that detects an electron backscatter diffraction pattern generated from the subject by irradiation with the electron beam. Furthermore, the electron microscope of the present embodiment includes a control analysis unit (control analyzer), and the control analysis unit includes operation control unit (operation controller or control circuit) that controls an operation of the subject holding unit, and a structure analysis unit (structure analyzer) that analyzes a crystal structure of the subject based on the electron backscatter diffraction pattern. A processor as programmed (programming that may be stored in one or more memories) can be configured to function as the control analysis unit or any of its components.

The subject holding unit is rotatable around an axis parallel to a direction of irradiation with the electron beam and is configured such that the subject installation surface is inclinable with respect to a plane perpendicular to the direction of irradiation with the electron beam. The structure analysis unit has a crystallinity evaluation unit that calculates a degree of similarity between the electron backscatter diffraction pattern and a crystal orientation based on a known crystal structure. The operation control unit controls a rotation operation and/or an inclination operation of the subject holding unit based on the degree of similarity.

Hereinafter, embodiments will be described with reference to the accompanying drawings.

Figure 1:
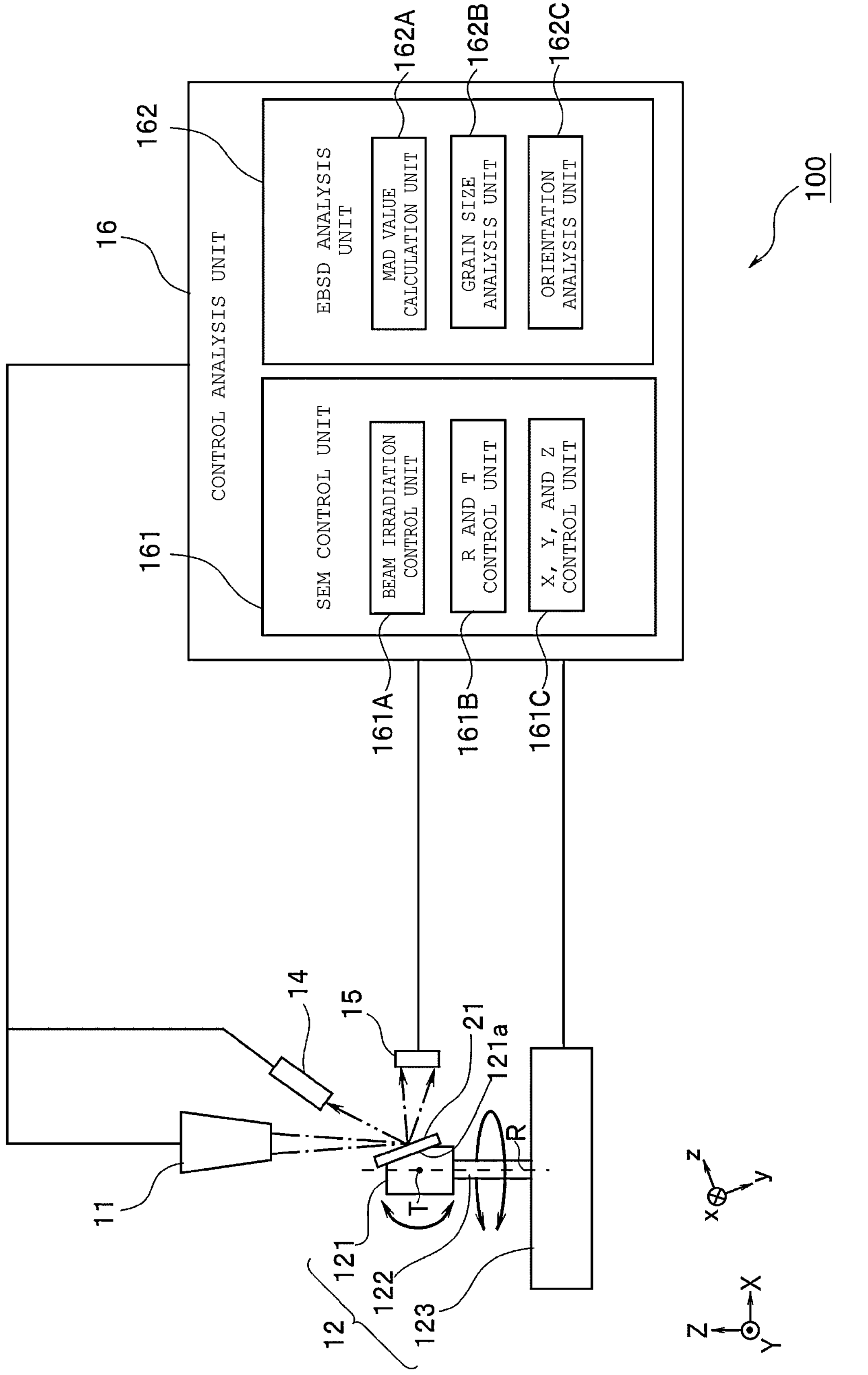
FIG. 1 is a block diagram showing a configuration example of an electron microscope according to at least one embodiment of the present disclosure.

FIG. 1 is a block diagram showing a configuration example of an electron microscope according to a first embodiment of the present disclosure. An electron microscope 100 of at least one embodiment is a scanning electron microscope (SEM). As shown in FIG. 1, the scanning electron microscope 100 includes an electron beam irradiation unit 11, a subject stage 12, a first detection unit 14, a second detection unit 15, and a control analysis unit 16.

The electron beam irradiation unit 11 generates an electron beam. Then, the electron beam irradiation unit 11 irradiates a subject 21 with the generated electrons. The electron beam irradiation unit 11 includes, for example, an electron source, a lens unit, and a scanning deflector. The electron source generates electrons. The electron source is, for example, an electron gun that accelerates electrons emitted from a cathode at an anode to emit an electron beam. The lens unit forms an electron probe (converged electron beam) by narrowing the electron beam emitted from the electron source. The lens unit can control the diameter of the electron probe and the probe current (irradiation current amount). The scanning deflector deflects the electron probe formed by the lens unit and moves the irradiation position on the subject 21. That is, the scanning deflector is used for scanning the subject 21 with the electron probe. In FIG. 1, a direction in which the electronic probe is applied to the subject 21 is referred to as a Z direction. In addition, in a plane perpendicular to the Z direction, two directions orthogonal to each other are referred to as an X direction and a Y direction, respectively.

The subject stage 12 includes a subject holding unit (or holder) 121, a support unit 122, and a base 123. The subject holding unit 121 has a subject installation surface 121*a*. The subject (object) 21 is placed on the subject installation surface 121*a*. Two directions orthogonal to each other in a plane parallel to the subject installation surface 121*a* are referred to as an x direction and a y direction, respectively, and a direction perpendicular to the subject installation surface 121*a* is referred to as a z direction. The subject stage 12 can move in the X direction, the Y direction, and the Z direction. In addition, the subject holding unit 121 can perform a rotation operation around a rotation axis R extending in the Z direction. Further, the subject holding unit 121 can also perform an inclination operation around an inclination axis T. The inclination axis T extends parallel to the XY plane and parallel to the subject installation surface 121*a* (xy plane). For example, in FIG. 1, the axis T extends in a direction from the front of the paper surface to the back of the paper surface in FIG. 1. The rotation operation can change the incident direction of the electron probe with respect to the subject installation surface 121*a* (xy plane).

The inclination operation can change the incident angle of the electron probe with respect to the subject installation surface 121*a* (xy plane).

The angle at which the subject holding unit 121 is rotationally moved from the initial state by the rotational operation is referred to as a rotation angle θr. For example, a state in which the subject installation surface 121*a* is installed parallel to the Y-axis is referred to as an initial state. In addition, the angle formed by the XY plane and the subject installation surface 121*a* (xy plane) is referred to as an inclination angle θt. For example, in the subject holding unit 121 shown in FIG. 1, the rotation angle θr is set to about 0°, and the inclination angle θt is set to about 70°. The position in the xy plane can be calculated from the position in the XY plane by considering the inclination angle θt and the rotation angle θr. For example, when the rotation angle θr is 0° and the inclination angle θt is 0°, the position in the xy plane and the position in the XY plane coincide with each other.

The first detection unit 14 detects the secondary electrons emitted from the subject 21 by irradiation with an electron beam. The subject 21 is scanned with an electron probe, and the secondary electrons emitted from the subject 21 are detected by the first detection unit 14, whereby an SEM image (secondary electron image) can be obtained.

The second detection unit 15 is an electron backscatter diffraction (EBSD) detector. The EBSD detector can detect an electron backscatter diffraction pattern generated from the subject 21 by irradiation with an electron beam. Hereinafter, the electron backscatter diffraction pattern detected by the second detection unit 15 is referred to as an EBSD image.

Figure 2A:
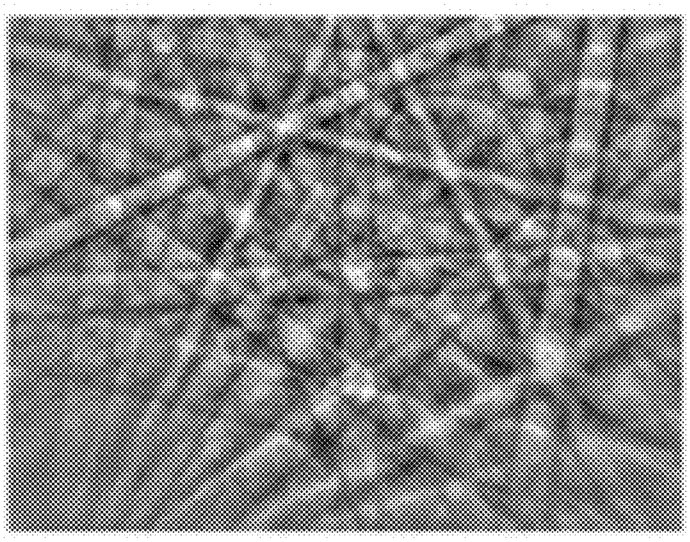
FIG. 2A is an image view of an EBSD image.
Figure 2B:
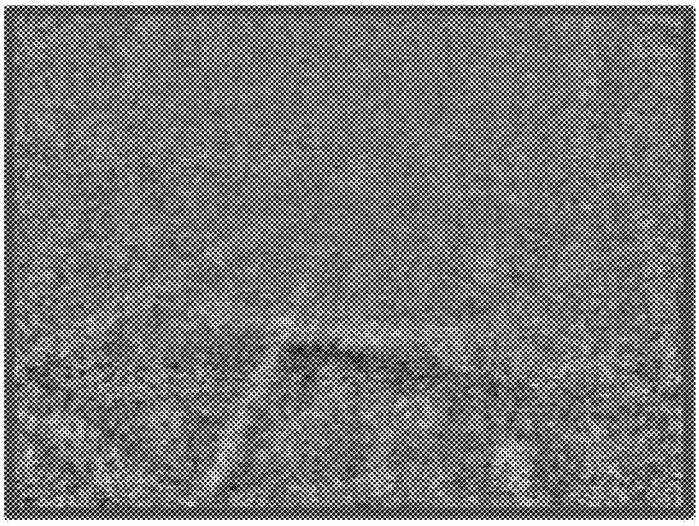
FIG. 2B is an image view of an EBSD image.

Generally, the electrons incident on a crystalline sample cause Bragg reflection (elastic scattering) after being subjected to inelastic scattering due to thermal vibration of atoms in the sample. As a result, the Kikuchi pattern is generated. The traveling direction of the electrons that have been subjected to inelastic scattering is distributed over a wide angle. Therefore, at the Bragg reflection position, a pair of a bright line and a dark line is generated by the reflection of the front surface and the rear surface of a certain crystal face. This pair of a bright line and a dark line is referred to as a Kikuchi line. The Kikuchi pattern is a pattern in which the real lattice of a crystal is projected, and the crystal orientation of a sample can be analyzed by performing crystal orientation indexing on the Kikuchi pattern. The EBSD image detected by the second detection unit 15 represents the Kikuchi pattern in the electronic probe irradiation area of the subject 21. FIG. 2A and FIG. 2B are image views of the EBSD images. In the EBSD image shown in FIG. 2A, the Kikuchi line, which is a pair of a bright line and a dark line, is clearly visible. On the other hand, in the EBSD image shown in FIG. 2B, the Kikuchi line is not clear. When the Kikuchi line appears clearly in the EBSD image detected by the second detection unit 15, it is possible to analyze the crystal orientation at the irradiation position of the electron probe.

The control analysis unit 16 includes an SEM control unit 161 and an EBSD analysis unit 162. The SEM control unit 161 includes a beam irradiation control unit 161A, an R and T control unit 161B, and an X, Y, and Z control unit 161C.

The beam irradiation control unit 161A controls the operation of the electron beam irradiation unit 11. For example, the beam irradiation control unit 161A controls the acceleration voltage of the electron, the diameter of the electron probe, the probe current amount, and the deflection state of the electron probe. The position and size of the irradiation area (hereinafter, referred to as a spot) of the electron probe in the subject 21 are set by controlling the electron beam irradiation unit 11. The R and T control unit 161B controls the rotation operation of the subject holding unit 121 such that the rotation angle θr of the subject holding unit 121 is a set angle. In addition, the R and T control unit 161B controls the inclination operation of the subject holding unit 121 such that the inclination angle θt of the subject installation surface 121*a* is a set angle. The X, Y, and Z control unit 161C controls the position of the subject holding unit 121. By moving the subject holding unit 121 in the X direction and/or the Y direction, an area (hereinafter, referred to as a small area) on the surface (xy plane) of the subject 21, which can be irradiated with the electron probe, can be moved.

The EBSD analysis unit 162 includes an MAD value calculation unit 162A, a grain size analysis unit 162B, and an orientation analysis unit 162C. The MAD value calculation unit 162A calculates the degree of similarity between the EBSD image detected by the second detection unit 15 and the theoretical Kikuchi pattern (hereinafter, referred to as a reflector) obtained from the known crystal structure. For example, the degree of similarity is calculated by the mean angular deviation (MAD) value, which is the average angular difference between the Kikuchi lines appearing in the EBSD image detected by the second detection unit 15 and the Kikuchi lines of the reflector. It can be said that the smaller the MAD value, the higher the degree of coincidence between the crystal orientation of the spot at which the EBSD image is acquired and the crystal orientation of the reflector. In the electron microscope of at least one embodiment, when the MAD value calculated by the MAD value calculation unit 162A is greater than a preset threshold value (for example, 0.5), it is determined that the EBSD image is not suitable for the evaluation of the crystallinity. The grain size analysis unit 162B detects the crystal grains present in the subject 21 and calculates the grain size of the detected crystal grains. For example, a set of continuous spots having the same crystal orientation is detected as a crystal grain. The orientation analysis unit 162C analyzes the orientation of the crystal grain.

The control analysis unit 16 may be incorporated in a computer having a central processing unit (CPU), a RAM, and a ROM. Each operation in the control analysis unit 16 may be performed in software by storing the operation in the control analysis unit 16 in advance in the memory as a program and executing the program in the CPU.

Figure 3:
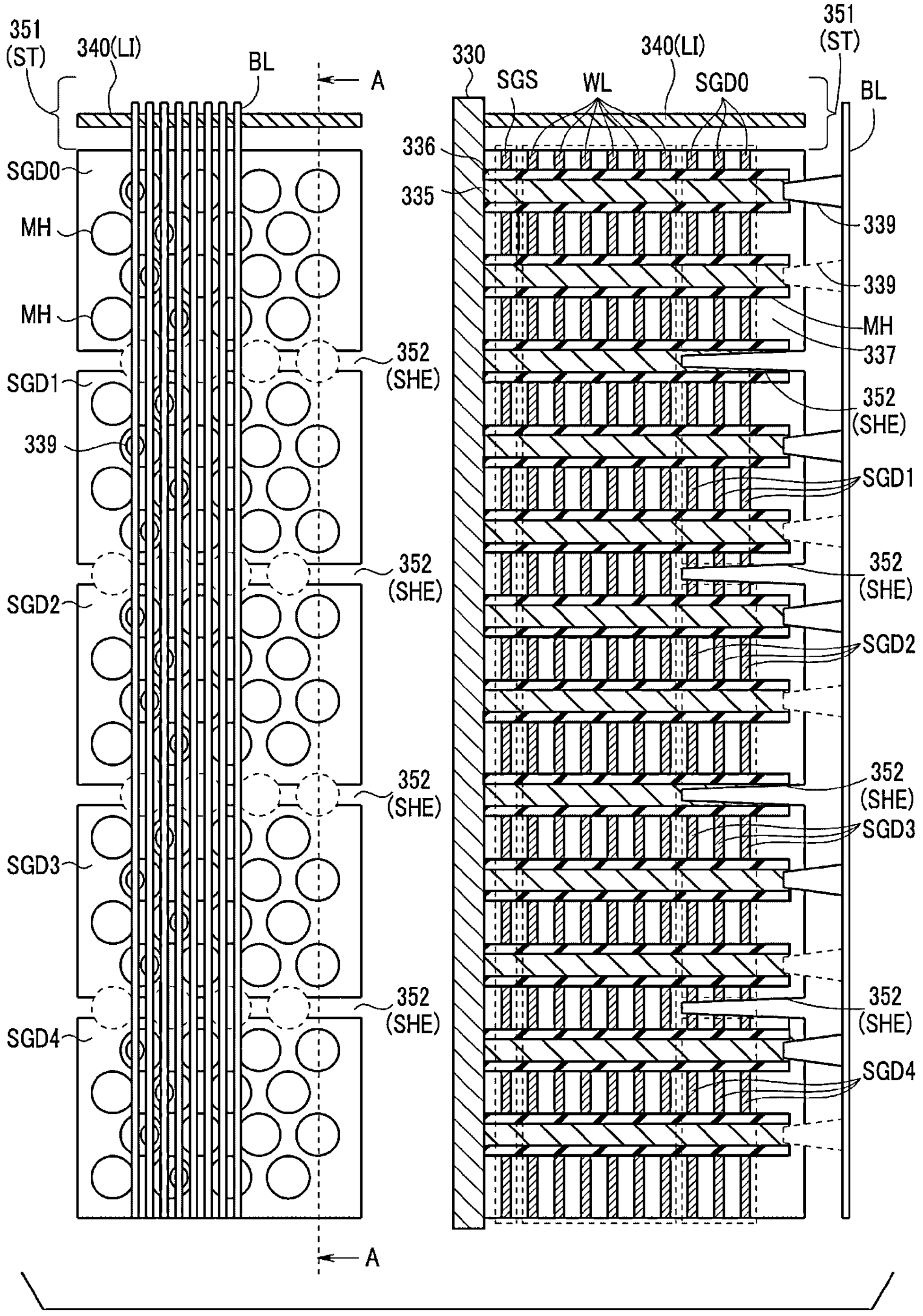
FIG. 3 is a plan view and a cross-sectional view illustrating a configuration example of a NAND flash memory cell array having a three-dimensional structure.

The electron microscope of the above-described embodiment can be used, for example, for the analysis of the grain size and the orientation of the crystal in a film or the like formed in the manufacturing process of a semiconductor device, such as a three-dimensional structure NAND memory. FIG. 3 is a plan view and a cross-sectional view illustrating a configuration example of a NAND flash memory cell array having a three-dimensional structure. The memory cell array includes a plurality of blocks. FIG. 3 shows one block of the plurality of blocks configuring the memory cell array. In addition, in FIG. 3, a part of a plan shape of the block is shown on the left side of the paper surface, and a cross-sectional shape taken along A-A line is shown on the right side of the paper surface. An insulating layer 351 separates one block BLK from the other block BLK. Specifically, as shown in the cross-sectional view on the right side of FIG. 3, the insulating layer 351 is extended from an upper surface of an interlayer insulating film 337 formed on a select gate line SGD to a source line 330, and separates the select gate line SGD, a plurality of word lines WL, and a select gate line SGS between the blocks BLK. The insulating layer 351 functions as a slit ST filled with an insulating material. A wiring 340 extending from an upper surface of the interlayer insulating film 337 to the source line 330 is formed in the insulating layer 351. The wiring 340 functions as a wiring LI, which is a connection wiring to the source line 330. The example of FIG. 3 shows an example in which five string units each including five select gate lines SGD0 to SGD4 separated by an insulating layer 352 are configured in one block. In the example on the right side of FIG. 3, the insulating layer 352 extends from the upper surface of the interlayer insulating film 337 formed on the select gate line SGD to between the lowest layer of the plurality of select gate lines SGD and the uppermost layer of the plurality of word lines WL, and separates the select gate lines SGD0 to SGD4 from each other. That is, the insulating layer 352 is a slit SHE filled with an insulating material. In FIG. 3, a case where the interlayer insulating film 337 is formed such that the upper surface of the interlayer insulating film 337 is located above an upper surface of a memory hole MH is shown as an example. However, the interlayer insulating film 337 may be formed such that the upper surface of the memory hole MH and the upper surface of the interlayer insulating film 337 have the same height.

Each memory hole MH in one string unit is connected to bit lines BL0, BL1, . . . (hereinafter, referred to as bit lines BL when there is no need to distinguish the bit lines BL0, BL1, . . . ) via a contact plug 339. In addition, on the left side of FIG. 3, only a part of the bit lines BL and a part of the contact plugs 339 are shown in consideration of the visibility of the drawing.

As shown in FIG. 3, each bit line BL is connected to one memory hole MH for each string unit via the contact plug 339. In order to connect each bit line BL to one memory hole MH of each string unit, the position of the contact plug 339 is shifted in the direction orthogonal to the extending direction of the bit line BL.

A plurality of NAND strings are formed on the source line 330. That is, the select gate line SGS, the plurality of word lines WL, and the plurality of select gate lines SGD are stacked on the source line 330 with an insulating film interposed therebetween. The memory hole MH reaching the source line 330 through the select gate line SGD, the word line WL, and the select gate line SGS is formed. On the side surface of the memory hole MH, an ONO film 336 configured with a block insulating film, a charge accumulation film (charge retention area), and a gate insulating film is formed, and a conductor column 335 is further embedded in the memory hole MH. The conductor column 335 is made of polysilicon, for example, and functions as an area where a channel is formed during the operation of the memory cell transistors and the select gate transistors provided in the NAND string.

The electron microscope of the embodiment can be used, for example, for the analysis of the grain size and the orientation of the crystal in a film (a polycrystalline silicon film, a metal film, a metal silicide film, or the like) that configures the select gate lines SGD and SGS, the word line WL, or the like, or a metal film that configures the bit line BL or the like.

Figure 4:
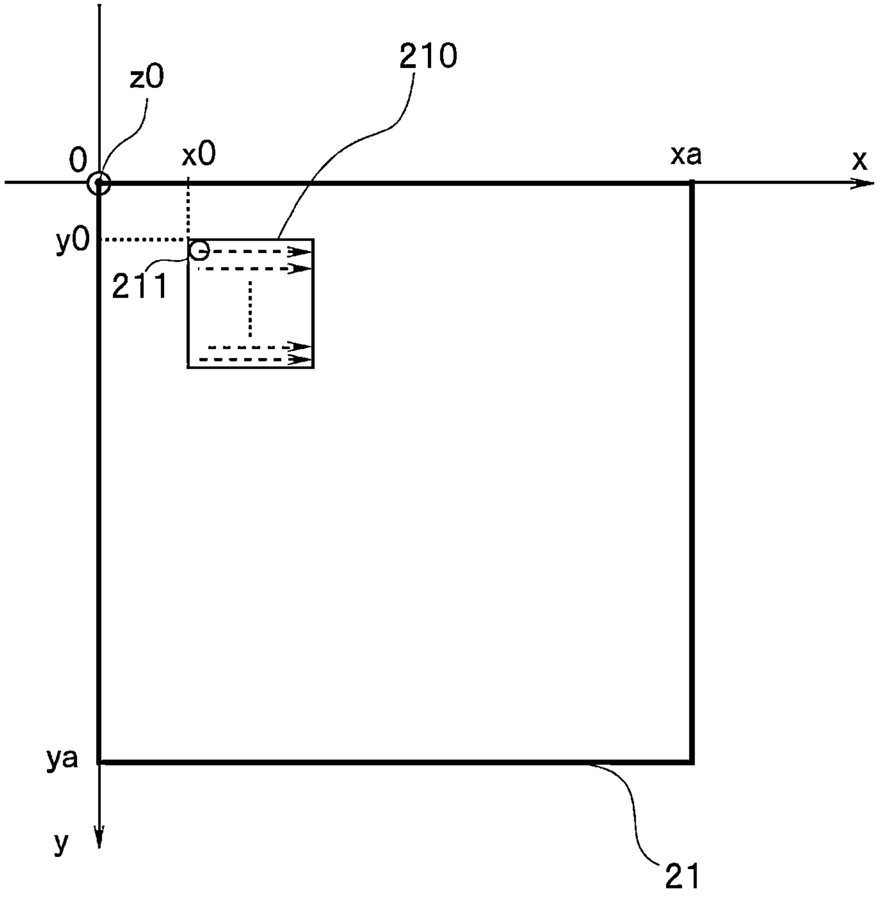
FIG. 4 is a view showing a small area and a spot set in a subject.

Next, a small area and a spot set in the subject 21 will be described. FIG. 4 is a view showing a small area and a spot set in a subject. In FIG. 4, an xy plane on the surface of the subject 21 is shown. The distance in the z direction from the surface of the subject 21 is referred to as z0. When the subject 21 is observed, first, a small area 210 is set on the surface of the subject 21. At this time, the range in which the electron probe can be scanned by only controlling the scanning angle with the scanning deflector without moving the subject holding unit 121 is set as the small area 210. For example, the size of the small area 210 is about 25 μm×25 μm. As shown in FIG. 4, for example, a rectangular area having x=x0 and y=y0 as one vertex is set as the small area 210. A spot 211, which is an irradiation area of the electron probe, is set in the small area 210. For example, the size of the spot 211 is about several nm to several tens of nm. For example, the SEM image can be acquired by completely scanning the small area 210 with an electron probe while moving the position of the spot 211 using the scanning deflector in a raster scan manner as shown by the dotted line with an arrow in FIG. 4. In addition, an EBSD image can be acquired for each spot 211. The position of the small area 210 is moved in the x direction and/or the y direction and/or the z direction, whereby an SEM image or an EBSD image can be acquired at any position on the surface of the subject 21.

Figure 5:
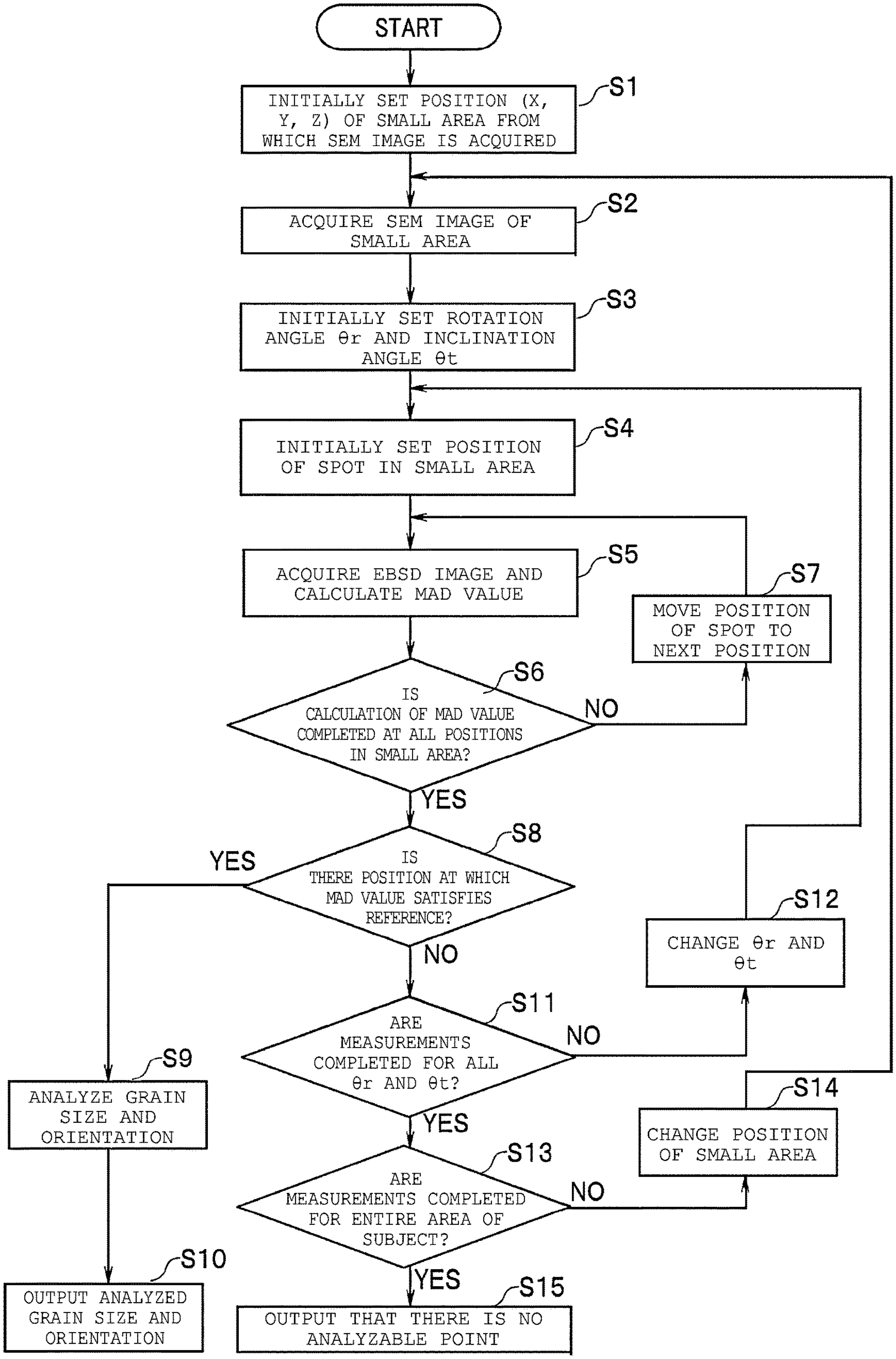
FIG. 5 is a flowchart showing an example of a procedure of a crystal evaluation method of at least one embodiment.

Next, a crystal evaluation method in the embodiment will be described. FIG. 5 is a flowchart showing an example of a procedure of a crystal evaluation method of an embodiment. By executing the procedure shown in FIG. 5, the crystallinity of the subject 21 can be analyzed efficiently and accurately.

First, the position (x, y, z) of the small area 210 from which the SEM image is acquired is initially set (S1). For example, as shown in FIG. 4, a rectangular area in which the position of one vertex is (x, y, z)=(x0, y0, z0) is used as the small area 210 from which the SEM image is acquired first. Next, an SEM image of the set small area 210 is acquired (S2). Next, the rotation angle θr and the inclination angle θt of the subject holding unit 121 are initially set (S3). In S3, for example, the rotation angle θr is set to 0° and the inclination angle θt is set to 70°. Subsequently, in the small area 210 in which the SEM image is acquired in S2, the position of the spot 211 for acquiring the EBSD image is initially set (S4). In S4, for example, at the time of acquiring the SEM image of S2, the position where the scanning of the electron probe is started is set as the initial position of the spot 211.

Subsequently, the spot 211 set in S4 is irradiated with an electron probe to acquire an EBSD image, and the MAD value is calculated (S5). When there is a position at which the EBSD image is not acquired, in the small area 210 in which the SEM image is acquired in S2 (S6, NO), the process proceeds to S7. In S7, the position of the spot 211 is moved to a position where the EBSD image is not acquired. For example, the position of the spot 211 is moved in the scanning order of the electron probe when the SEM image of S2 is acquired. After the position of the spot 211 is moved, the process returns to S5, and the EBSD image is acquired and the MAD value is calculated.

Meanwhile, in the small area 210 from which the SEM image is acquired in S2, when the EBSD image is acquired and the calculation of the MAD value is completed for all positions to be irradiated with the electron probe (S6, YES), the process proceeds to S8. In S8, it is determined whether there is a position at which the MAD value satisfies the set reference among all the positions in the small area 210. For example, when the MAD value is equal to or less than a set threshold value (for example, 0.5), the position is determined to satisfy the reference. The position that satisfies the reference is suitable for evaluating the crystallinity because the degree of coincidence between the crystal orientation of the spot at which the EBSD image is acquired and the crystal orientation of the reflector is high.

Figure 6A:
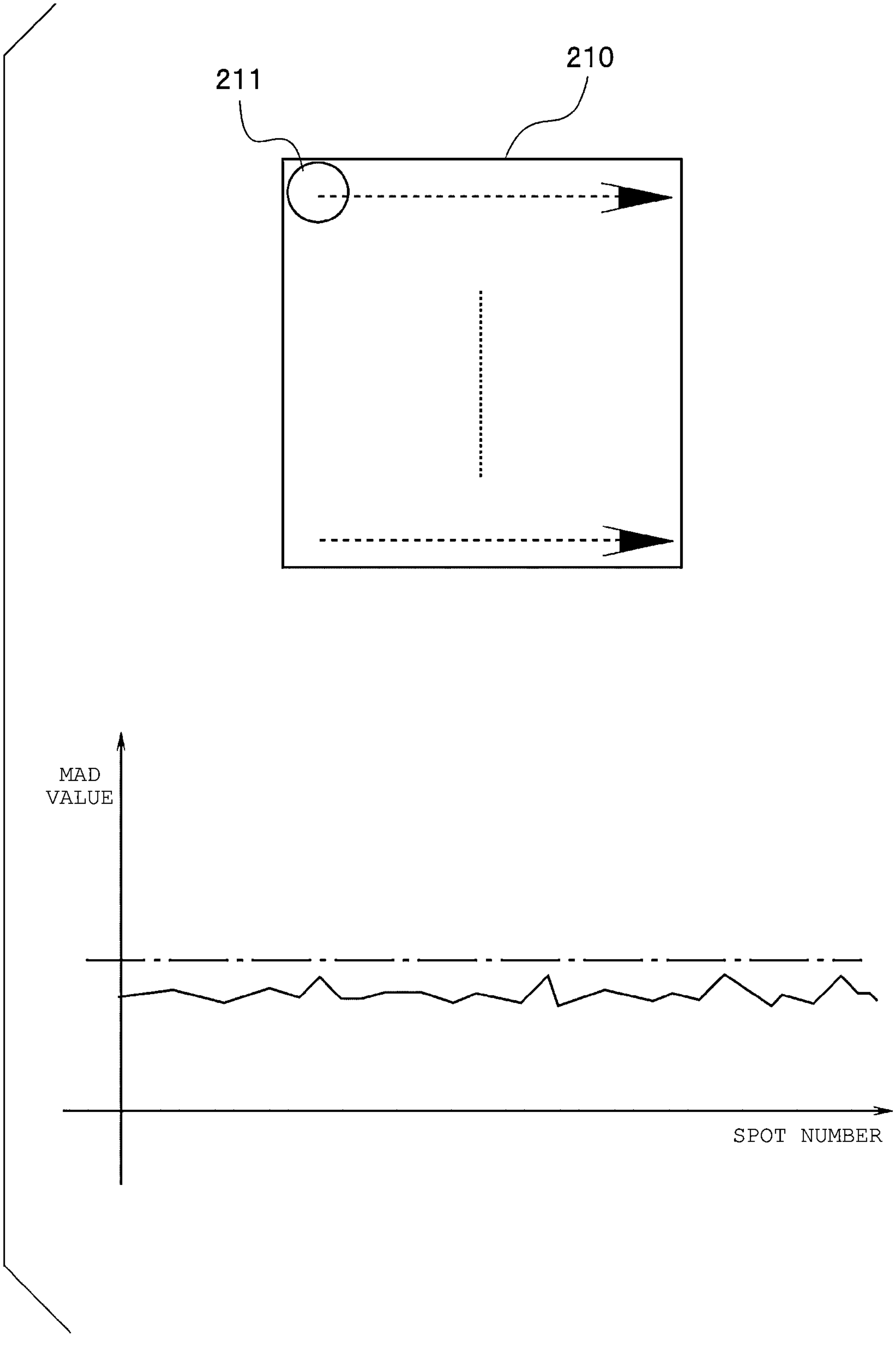
FIG. 6A is a diagram showing an example of a transition of an MAD value.
Figure 6B:
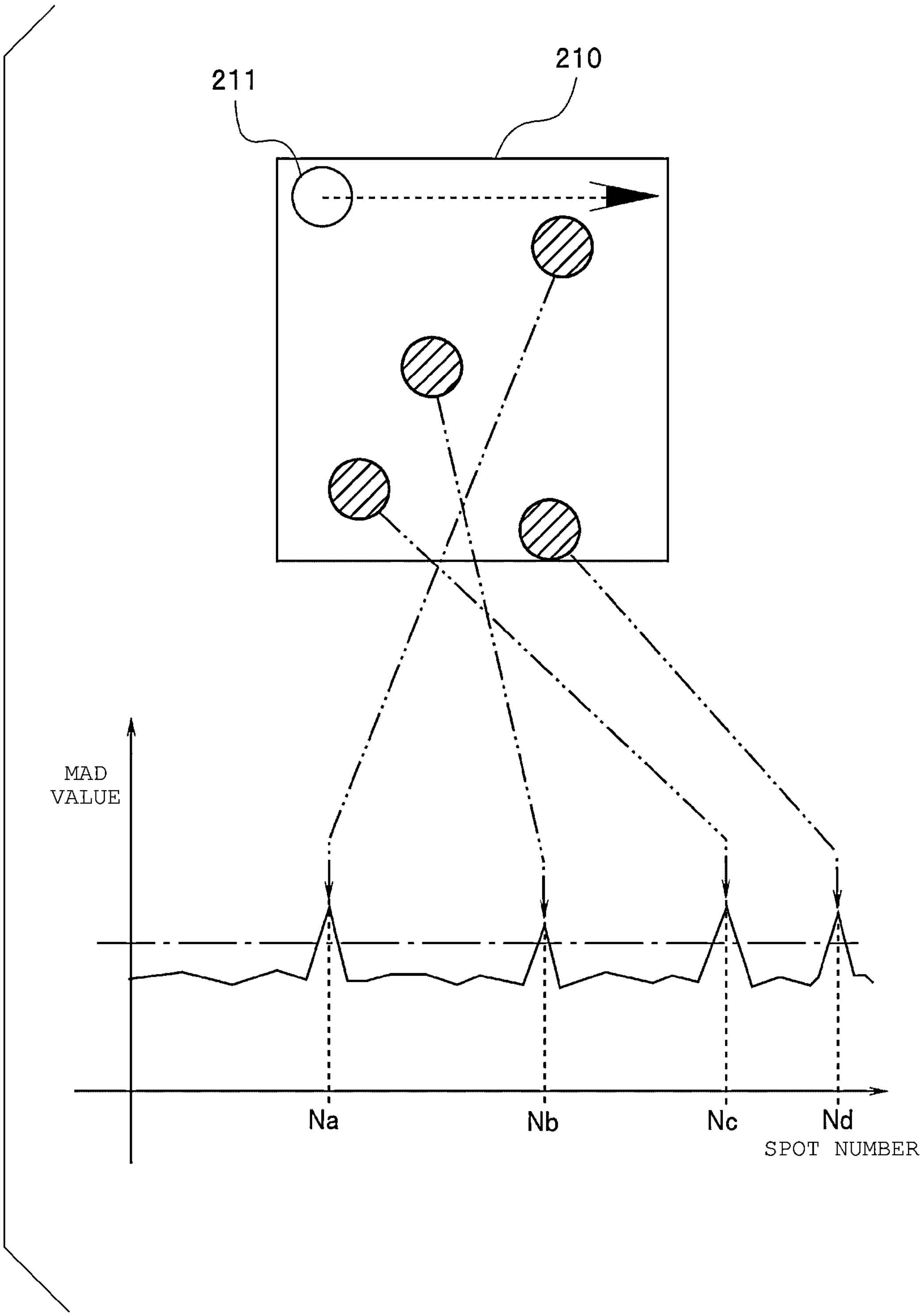
FIG. 6B is a diagram showing an example of a transition of an MAD value.

FIG. 6A and FIG. 6B are diagrams showing an example of a transition of an MAD value. In both of FIGS. 6A and 6B, the lower diagrams show the transition of the MAD value. In the lower diagram, the vertical axis represents the MAD value, and the higher the axis, the smaller the MAD value. In addition, in the lower diagram, the horizontal axis represents a spot number which is a measurement order of the spots. That is, the lower diagrams of FIGS. 6A and 6B are diagrams in which the MAD values are plotted in the order of calculation from the left side to the right side of the horizontal axis. The set threshold value is indicated by a one-dot chain line, and the MAD value plotted above the one-dot chain line satisfies the reference. In addition, in both of FIGS. 6A and 6B, the upper diagram shows the small area 210 and the spot 211 which are measurement targets.

FIG. 6A shows an example in which there is no MAD value satisfying the set reference when measurement is performed at a certain rotation angle θr and inclination angle θt. That is, even when the measurement is performed while moving the spot 211, there is no spot 211 in which the MAD value satisfies the set reference. Meanwhile, FIG. 6B shows an example in which there is the MAD value satisfying the set reference when measurement is performed at other rotation angle θr and inclination angle θt. That is, when the measurement is performed while moving the spot 211, the spot 211 (the spot indicated by the round mark with the hatching) in which the MAD value satisfies the set reference is detected. The correspondence between the position of the spot in the upper diagram and the MAD value in the lower diagram is shown by a two-dot chain line.

As shown in FIG. 6B, when there is a position at which the MAD value satisfies the set reference (S8, YES), the process proceeds to S9, and the crystal orientation is analyzed for each of the positions that satisfy the reference, and the grain size and the orientation are analyzed. For example, as shown in FIG. 6B, when four MAD values satisfy the reference, the crystal orientation is analyzed for each of the position of the Na-th spot, the position of the Nb-th spot, the position of the Nc-th spot, and the position of the Nd-th spot, and the grain size and the orientation are analyzed. Then, the analyzed grain size and orientation are output, and the series of measurement procedures are completed (S10).

Meanwhile, as shown in FIG. 6A, when there is no position at which the MAD value satisfies the set reference (S8, NO), regarding the small area 210, it is determined whether a series of measurements from the acquisition of the EBSD image to the calculation of the MAD value are completed for all of the rotation angles θr and the inclination angles θt (S11). All the rotation angles θr in S11 are rotation angles θr that may be set within a preset range. Similarly, all the inclination angles θt in S11 are the inclination angles θt that may be set within a preset range. For example, when the setting range of the inclination angle is 68° to 73° and the minimum setting angle is 1°, all the inclination angles θt refer to six angles of 68°, 69°, 70°, 71°, 72°, and 73°.

Even in an area having crystallinity, the detection intensity of the Kikuchi line varies depending on the incident direction or the incident angle of the electron probe. That is, as shown in FIG. 2B, it is considered that an area in which an unclear EBSD image is detected is amorphous, or has crystallinity but has a low detection intensity depending on the incident conditions of the electron probe. Therefore, by changing the incident direction and the incident angle of the electron probe and acquiring the EBSD image again for the small area 210 at the same position, the overlooking of the area having crystallinity can be prevented and the accuracy of the analysis can be improved.

With respect to the small area 210, when there are the rotation angle θr and the inclination angle θt for which a series of measurements from the acquisition of the EBSD image to the calculation of the MAD value are not completed (S11, NO), the process proceeds to S12, and the rotation angle θr and the inclination angle θt are changed. In the changed state, a series of procedures from S4 to S8 are executed to search whether there is an area having crystallinity in the small area 210. Meanwhile, with respect to the small area 210, when a series of measurements from the acquisition of the EBSD image to the calculation of the MAD value are completed for all the rotation angles θr and the inclination angles θt (S11, YES), the process proceeds to S13, and it is determined whether a series of measurements from the acquisition of the EBSD image to the calculation of the MAD value are completed for the entire area of the subject 21.

When there is an unmeasured area (S13, NO), the position of the small area 210 is changed such that the unmeasured area is provided in the small area 210 (S14). A series of procedures from S2 to S11 are executed for the small area 210 after the position is changed to search whether there is an area having crystallinity in the small area 210. Meanwhile, when the measurement of the entire area of the subject 21 is completed (S13, YES), it is output that there is no area suitable for the evaluation of the crystallinity in the subject 21 (S15), and the series of measurement procedures are completed.

As described above, according to the present embodiment, the EBSD image of each spot is acquired while moving the position of the spot on the subject 21. The MAD value of each EBSD image is calculated to determine an area suitable for the evaluation of the crystallinity, and the grain size and the orientation are analyzed. When there is no area in which the MAD value is smaller than the reference value, the rotation angle and the inclination angle of the subject holding unit 121 are changed, and an area suitable for the evaluation of the crystallinity is searched while changing the incident angle and the incident direction of the electron probe. As a result, it is possible to provide an electron microscope and a crystal evaluation method capable of preventing the overlooking of an area having crystallinity and capable of efficiently and accurately analyzing the crystallinity.

While certain embodiments have been described, these embodiments have been presented by way of example only, and are not intended to limit the scope of the disclosure. Indeed, the novel embodiments described herein may be embodied in a variety of other forms; furthermore, various omissions, substitutions and changes in the form of the embodiments described herein may be made without departing from the spirit of the disclosure. The accompanying claims and their equivalents are intended to cover such forms or modifications as would fall within the scope and spirit of the disclosure.

What is claimed is:

1. An electron microscope comprising:

a subject holder having a subject installation surface on which the subject having a surface is placed;

an electron beam irradiation source configured to irradiate, with an electron beam, an irradiation area of the surface of the subject;

a first detector configured to detect secondary electrons emitted from the subject by irradiation with the electron beam;

a second detector configured to detect an electron backscatter diffraction pattern generated from the subject by irradiation with the electron beam; and a control analyzer including:

an operation controller configured to control an operation of the subject holder, and a structure analyzer configured to analyze a crystal structure of the subject based on the electron backscatter diffraction pattern, wherein the subject holder is rotatable around an axis parallel to a direction of irradiation with the electron beam and is able to incline the subject installation surface relative to a plane perpendicular to the direction of irradiation with the electron beam, the structure analyzer having a crystallinity evaluator configured to calculate a degree of similarity between the electron backscatter diffraction pattern and a crystal orientation based on a known crystal structure, and the operation controller configured to control at least one of a rotation operation or an inclination operation of the subject holder based on the degree of similarity, wherein the degree of similarity is an MAD value which is an average angular difference between a Kikuchi line of the electron backscatter diffraction pattern and a Kikuchi line of the known crystal structure, wherein the subject has a small area, the small area having a plurality of the irradiation areas and set in the subject, the crystallinity evaluator configured to calculate the MAD value for each of the electron backscatter diffraction patterns detected from each of the plurality of irradiation areas, and the operation controller configured to control the at least one of the rotation operation or the inclination operation of the subject holder when all the MAD values for the electron backscatter diffraction patterns are greater than a predetermined threshold value.

2. The electron microscope according to claim 1, wherein the electron backscatter diffraction pattern detected from the same irradiation area is detected before and after the at least one of the rotation operation or the inclination operation in the subject is performed.

3. The electron microscope according to claim 1, wherein the electron beam irradiation source includes an electron source configured to generate electrons.

4. The electron microscope according to claim 3, wherein the electron source includes an electron gun.

5. The electron microscope according to claim 3, wherein the electron beam irradiation source includes a lens configured to focus the electron beam.

6. The electron microscope according to claim 3, wherein the electron beam irradiation source includes a scanning deflector configured to deflect the electron beam.

7. The electron microscope according to claim 1, further comprising a grain size analyzer configured to detect crystalline grain size in the subject.

8. A crystal evaluation method comprising:

irradiating with an electron beam an irradiation area of a surface of a subject placed on a subject installation surface of a subject holder;

detecting an electron backscatter diffraction pattern generated from the subject by irradiation with the electron beam;

calculating a degree of similarity between the electron backscatter diffraction pattern and a crystal orientation based on a known crystal structure; and controlling at least one of a rotation operation or an inclination operation of the subject holder based on the degree of similarity, the subject holder being rotatable around an axis parallel to a direction of irradiation with the electron beam and able to incline the subject installation surface relative to a plane perpendicular to the direction of irradiation with the electron beam, wherein the degree of similarity is an MAD value which is an average angular difference between a Kikuchi line of the electron backscatter diffraction pattern and a Kikuchi line of the known crystal structure, wherein the subject has a small area, the small area having a plurality of the irradiation areas and set in the subject, wherein the method further comprises:

calculating the MAD value for each of the electron backscatter diffraction patterns detected from each of the plurality of irradiation areas and controlling the at least one of the rotation operation or the inclination operation of the subject holder when all the MAD values for the electron backscatter diffraction patterns are greater than a predetermined threshold value.

* * * * *